(12) United States Patent
Hsu et al.

(10) Patent No.: US 11,508,566 B2
(45) Date of Patent: Nov. 22, 2022

(54) USE OF ANTHRANILIC ACID DERIVATIVE AS MATRIX FOR MALDI MASS SPECTROMETRY

(71) Applicant: National Taiwan University, Taipei (TW)

(72) Inventors: Cheng-Chih Hsu, Taipei (TW); Pi-Tai Chou, Taipei (TW); Chuping Lee, Taipei (TW); Peng-Hsuan Huang, Taipei (TW); Li-En Lin, Taipei (TW); Chun-Ying Huang, Taipei (TW); Ta-Chun Lin, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 17/011,460

(22) Filed: Sep. 3, 2020

(65) Prior Publication Data

US 2021/0066060 A1  Mar. 4, 2021

Related U.S. Application Data

(60) Provisional application No. 62/894,981, filed on Sep. 3, 2019.

(51) Int. Cl.
*G01N 33/48* (2006.01)
*H01J 49/16* (2006.01)
(Continued)

(52) U.S. Cl.
CPC .......... *H01J 49/164* (2013.01); *C07C 223/06* (2013.01); *C07C 229/56* (2013.01);
(Continued)

(58) Field of Classification Search
CPC ... C07C 223/06; C07C 229/56; C07C 233/33; C07C 2601/16; G01N 33/4833; H01J 49/0004; H01J 49/004; H01J 49/164
(Continued)

(56) References Cited

U.S. PATENT DOCUMENTS 5,783,577 A * 7/1998 Houghten ............ C07D 239/90
436/111
9,305,756 B2   4/2016 Becker et al.
(Continued)

OTHER PUBLICATIONS

Zhang; et al., "Matrix-Assisted Laser Desorption/Ionization Mass Spectrometry Methods for Oligodeoxynucleotides: Improvements in Matrix, Detection Limits, Quantification, and Sequencing" J Am Soc Mass Spectrom 2000, 11, pp. 854-865 (Year: 2000).*
(Continued)

*Primary Examiner* — Wyatt A Stoffa
(74) *Attorney, Agent, or Firm* — Loeb & Loeb LLP

(57) ABSTRACT

A use of an anthranilic acid derivative as a matrix for a MALDI Mass spectrometry, comprising:
preparing a matrix compound represented by the following formula:

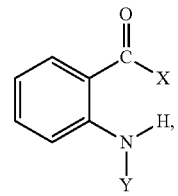

wherein X is selected from hydrogen and a hydroxyl group, and Y is selected from hydrogen, a methyl group or an acetyl group, provided that when X is hydrogen, Y is hydrogen or an acetyl group, and when X is a hydroxyl group, Y is a methyl group;
applying the matrix compound and an analyte onto a sample holder; and
analyzing the analyte by the MALDI mass spectrometer.

15 Claims, 8 Drawing Sheets

(51) Int. Cl.
  *C07C 223/06* (2006.01)
  *C07C 233/33* (2006.01)
  *H01J 49/00* (2006.01)
  *G01N 33/483* (2006.01)
  *C07C 229/56* (2006.01)

(52) U.S. Cl.
  CPC ....... *C07C 233/33* (2013.01); *G01N 33/4833* (2013.01); *H01J 49/0004* (2013.01); *H01J 49/004* (2013.01); *C07C 2601/16* (2017.05)

(58) Field of Classification Search
  USPC ........................................................ 250/281
  See application file for complete search history.

(56) References Cited

U.S. PATENT DOCUMENTS

| | | |
|---|---|---|
| 11,285,831 B1 * | 3/2022 | Youssefzadeh ......... B60L 53/14 |
| 2005/0158863 A1 | 7/2005 | Stahl et al. |
| 2014/0206094 A1 | 7/2014 | Amano et al. |
| 2022/0089643 A1 * | 3/2022 | Beswick ................ A61K 47/55 |

OTHER PUBLICATIONS

Huang, P., Huang, C. Y., Lin, T. C., Lin, L. E., Yang, E., Lee, C., . . . & Chou, P. T. (2020). Toward the rational design of universal dual polarity matrix for MALDI mass spectrometry. Analytical Chemistry, 92(10), 7139-7145. (Year: 2020).*

* cited by examiner

USE OF ANTHRANILIC ACID DERIVATIVE AS MATRIX FOR MALDI MASS SPECTROMETRY

CROSS-REFERENCE TO RELATED PATENT APPLICATION

This application claims the benefit under 35 U.S.C. § 119 of U.S. Provisional Patent Application Ser. No. 62/894,981 filed on Sep. 3, 2019, which is incorporated herein by reference in its entirety.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a use of an anthranilic acid derivative as a matrix for a MALDI Mass spectrometry, and more particularly to a use of an anthranilic acid derivative as a universal dual polarity matrix for a MALDI Mass spectrometry.

BACKGROUND

Matrix-assisted laser desorption/ionization time-of-flight (MALDI-TOF) MSI provides high spatial resolution and is applicable for analyzing wide variety of biomolecules simultaneously, which has been applied to, for example, determine biomarkers of diseases and track target molecule such as administered drugs. Among the biomolecules, lipids are essential building blocks for cells and storage of energy while playing essential roles in many biological functions, including cell signaling. The abundances of lipids are highly correlated with many diseases. Changes of lipid localizations and profiles are key features of these diseases, such as cancer, metabolic diseases and neurodegenerative diseases. Therefore, techniques for molecular imaging of lipid species in tissues are important to gain the molecular insight into biochemical mechanisms and to the clinical evaluation of the disease status. Among these techniques, mass spectrometry imaging (MSI) is a powerful tool for showing spatial localization of the molecules.

Lipids have diverse chemical structures and many of them may only be measured in one polarity, for example, in positive or negative ion mode by the MALDI Mass spectrometry. For example, phosphatidylcholines (PC) are typically observed as positive ions, whereas many other lipids, such as phosphatidic acids (PA), phosphatidylserines (PS), phosphatidylinositols (PI) and sulfatides (ST) are usually observed as negative ions in MALDI-TOF MSI. However, most commercial MALDI matrices are only suitable for single polarity detection. For example, 2,5-dihydroxybenzoic acid (2,5-DHB) and α-cyano-4-hydroxybenzoic acid (CHCA) are most often used in positive ion detection because their carboxyl group acts as a proton donor, whereas 9-aminoacridine (9-AA) is favored in negative ion detection because its amine group acts as the proton acceptor. A dual polarity MALDI matrix is one approach that allows universal mass spectrometric analysis of both positively and negatively charged lipid species on one sample.

Researchers have discovered a few dual-polarity matrices suitable for MALDI MSI at high spatial resolution. One early example is 1,5-diaminonaphthalene (1,5-DAN) proposed by Thomas et al (Molin, L.; Seraglia, R.; Dani, F. R.; Moneti, G.; Traldi, P. Rapid Commun. Mass Spectrom. 2011, 25, 3091 3096; Thomas, A.; Dé glon, J.; Lenglet, S.; Mach, F.; Mangin, P.; Wolfender, J.-L.; Steffens, S.; Staub, C. Anal. Chem. 2010, 82, 6687-6694; and Thomas, A.; Charbonneau, J. L.; Fournaise, E.; Chaurand, P. Anal. Chem. 2012, 84, 2048-2054) and, more recently, 3-aminophthalhydra-zide (luminol) proposed by Li et al (Li, B.; Sun, R.; Gordon, A.; Ge, J.; Zhang, Y; Li, P.; Yang, H. Anal. Chem. 2019, 91, 8221-8228). However, in both cases, only MSI results of lipids and small metabolites are shown. Their effectiveness for protein and peptide detection are not demonstrated. More interestingly, neither of the two compounds possess a carboxylic group for enhanced ionization efficiency in positive ion mode.

In addition, US patent application publication No. 2014/0206094A1, entitled "MALDI MASS SPECTROMETRY METHOD", discloses a plurality of matrices for achieving desorption and ionization of molecules to be analyzed which includes 1,8-Diaminonaphthalene (1,8-DAN), 1,5-Diaminonaphthalene (1,5-DAN), 2,5-Dihydroxybenzoic acid (DHBA), anthranilic acid, nicotinic acid, etc. U.S. Pat. No. 9,305,756B2, entitled "PREPARATION ENHANCEMENTS AND METHODS OF USE FOR MALDI MASS SPECTROMETRY", discloses several matrix suitable for use for MADLI MS, which may include 3-hydroxypicolinic acid (3-HPA), 2,5-dihydroxybenzoic acid (DHB), alpha-cyano-4-hydroxycinnamic acid (alpha-CHCA), picolinic acid (PA), 3-aminopicolinic acid, 3-picolinic acid, 2,4,6-trihydroxyacetophenone (THAP), anthranilic acid, nicotinic acid and the like. US patent application publication No. 2005/0158863 A1, entitled "MALDI-MATRIX", discloses matrices that are made up of a salt of an amine reacting as a proton acceptor and an organic substance reacting as a proton donor, and the amine may be a primary amine, a secondary or tertiary amine to whose N atom may be bound to 1 to 3 residues. However, as stated above, these publications still fail to specifically propose a novel matrix for lipid or protein analysis which allows universal mass spectrometric analysis on both positive and negative ion mode.

Accordingly, there is still a need to provide suitable matrices for both positive and negative ion detection in MALDI-TOF imaging, i.e., dual polarity matrices for the detection of biomolecules, such as lipids.

SUMMARY

In response to the above-referenced technical inadequacies, the present disclosure provides a use of a series of anthranilic acid derivatives to be candidates of the matrix for a MALDI Mass spectrometry. The use of these specific matrix compounds is to be adapted to different sample preparation processes and yields satisfied efficiency in analysis by a MALDI Mass spectrometry.

In one aspect, the present disclosure provides a use of an anthranilic acid derivative as a matrix for a MALDI Mass spectrometry, comprising:

preparing a matrix compound represented by the following formula:

wherein X is selected from hydrogen and a hydroxyl group, and Y is selected from hydrogen, a methyl group or an acetyl group, provided that when X is hydrogen, Y is hydrogen or an acetyl group, and when X is a hydroxyl group, Y is a methyl group;

applying the matrix compound and an analyte onto a sample holder; and analyzing the analyte by the MALDI mass spectrometer.

BRIEF DESCRIPTION OF THE DRAWINGS

The present disclosure will become more fully understood from the following detailed description and accompanying drawings.

DETAILED DESCRIPTION

The present disclosure is more particularly described in the following examples that are intended as illustrative only because numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles are used herein for the convenience of a reader, which shall have no influence on the scope of the present disclosure.

The terms used herein generally have their ordinary meanings in the art. In the case of conflict, the present document, including any definitions given herein, will prevail. The same thing may be expressed in more than one way. Alternative language and synonyms may be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" may be used to describe various components or the like, which are for distinguishing one component from another one only, and are not intended to, nor should be construed to impose any substantive limitations on the components or the like.

The present disclosure provides a use of an anthranilic acid derivative as a matrix for a MALDI Mass spectrometry, comprising the following steps:

(a) preparing a matrix compound represented by the following formula:

wherein X is selected from hydrogen and a hydroxyl group, and Y is selected from hydrogen, a methyl group or an acetyl group, provided that when X is hydrogen, Y is hydrogen or an acetyl group, and when X is a hydroxyl group, Y is a methyl group;

(b) applying the matrix compound and an analyte onto a sample holder; and (c) analyzing the analyte by the MALDI mass spectrometer.

In the present disclosure, the matrix candidates, i.e., the matrix compound used in step (a), may be determined by a rational design approach before synthesis and experimentation. An ideal matrix for lipid analysis has: (i) high absorption coefficient at a commercial laser wavelength, (ii) simple and low matrix background below 1000 Da and (iii) ability to observe both positive and negative lipid ions. A dual polarity MALDI matrix thus allows universal mass spectrometric analysis of both positively- and negatively-charged lipid species within one single measurement. To achieve this purpose, rational design of the functional groups on the core light-absorbing structures is adopted to search for the matrix candidates.

The inventors of the present disclosure thereby designed and synthesized a series of matrix compounds I to IV containing a simple aniline derivative anchored by a carboxyl group for COOH—$NH_2$ (compound I) and COOH—NHMe (compound IV), and formyl group for CHO—$NH_2$ (compound II), and CHO—NHAc (compound III). The synthesis of matrix compounds II to IV (the Synthesis Examples) and other compounds V to IX (the Comparative Examples) are described in details below.

SYNTHESIS EXAMPLES

Synthesis of 2-aminobenzaldehyde (CHO—$NH_2$, Compound II)

To a solution of anthranilic acid (1.0 g, 7.30 mmol) in dry THF (20 mL) was added dropwise a solution of lithium aluminum hydride (LAH) in THF (2.4M, 4.6 mL, 11.04 mmol) while the temperature was maintained at −30° C. with stirring. The resulting mixture was warmed to room temperature and stirred in the same temperature for additional 6 h. Until the end of the reaction, the mixture was hydrolyzed by addition of water (20 mL) and 5% NaOH (2.0 mL). The resulting suspension was extracted with EtOAc (3×50 mL). The combined organic layer was dried over anhydrous $MgSO_4$.

The dried organic solution was then filtered and concentrated under reduced pressure. The residue was recrystallized from ethyl acetate and hexane, affording the corresponding 2-aminobenzyl alcohol quantitatively as a white solid. A solution of 2-aminobenzyl alcohol (0.70 g, 5.68 mmol) was dissolved in DCM (50 mL). Manganese (IV) oxide (3.95 g, 45.43 mmol) was added and the reaction mixture was stirred at room temperature for about 12 h. Manganese (IV) oxide was filtered off and the resulting filtrate was concentrated under reduced pressure. The residue was purified by column chromatography on silica gel (hexane:EtOAc=10:1) to afford CHO—$NH_2$ (II) (0.46 g, 67%) as yellow solid. $^1$H NMR (400 MHz, DMSO-$d_6$, 298 K) δ (ppm): 9.81 (s, 1H), 7.52 (d, J=8.0 Hz, 1H), 7.30 (t, J=8.0 Hz, 1H), 7.11 (b, 1H), 6.75 (d, J=8.0 Hz, 1H), 6.64 (t, J=8.0 Hz, 1H); $^{13}$C NMR (100 MHz, DMSO-$d_6$, 298 K) δ (ppm): 193.97, 150.66, 135.55, 135.04, 117.74, 115.80, 114.91.

Synthesis of N-(2-formylphenyl)acetamide (CHO—NHAc, Compound III)

Figure 1A:
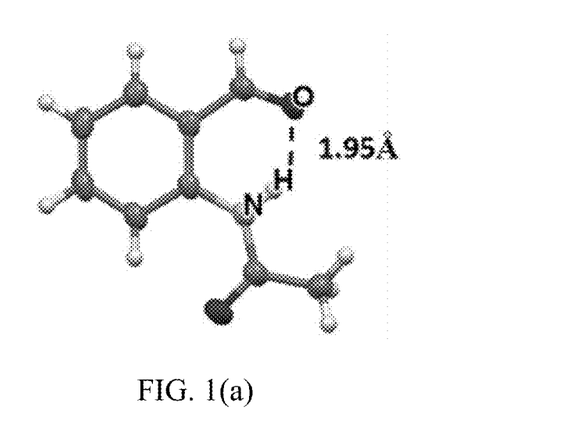
FIG. 1(a) shows a schematic view of the molecular structure of an anthranilic acid derivatives to be used as a matrix for MALDI Mass spectrometry.

2-Aminobenzaldehyde (compound II, 0.3 g, 2.48 mmol), acetic anhydride (0.33 g, 3.22 mmol) and triethylamine (TEA, 0.376 g, 3.72 mmol) were dissolved in $CHCl_3$ (15 mL). The mixture was refluxed at 60° C. for 24 h. After being cooled to room temperature, the reaction mixture was poured into water (60 mL), and the aqueous layer was extracted with $CHCl_3$ (3×30 mL). The combined organic layer was washed with 1M HCl (60 mL) and dried over anhydrous $MgSO_4$. The dried organic solution was filtered and concentrated under reduced pressure. The residue was purified by column chromatography on silica gel (hexane: $CH_2Cl_2$=5:1) to afford CHO—NHAc (III) (0.235 g, 58%) as white solid. $^1$H NMR (400 MHz, DMSO-$d_6$, 298 K) δ (ppm): 10.71 (b, 1H), 9.96 (s, 1H), 8.10 (d, J=8.0 Hz, 1H), 7.84 (d, J=12.0 Hz, 1H), 7.66 (m, 1H), 7.30 (m, 1H), 2.15 (s, 3H); 13C NMR (100 MHz, DMSO-$d_6$, 298 K) δ (ppm): 193.9, 169.2, 139.8, 135.2, 132.8, 124.4, 123.8, 121.1, 24.3. The molecular structure (X-ray) of the synthesized matrix compound III is shown in FIG. 1(a), which is in a planar configuration.

Synthesis of 2-(methylamino)benzoic acid (COOH—NHMe, Compound IV)

Figure 1B:
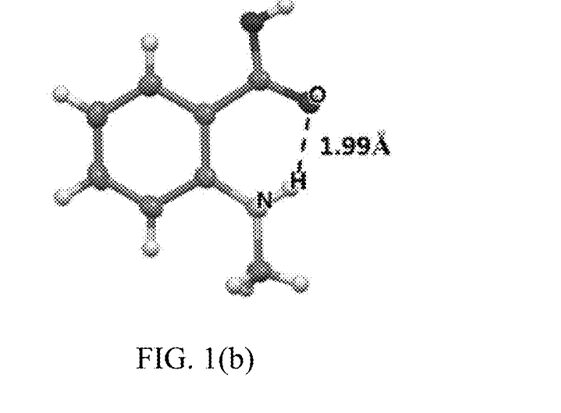
FIG. 1(b) shows a schematic view of the molecular structure of another anthranilic acid derivatives to be used as a matrix for MALDI Mass spectrometry.

To a solution of sodium carbonate (4.0 g, 37.9 mmol) in water (70 mL) was added anthranilic acid (I, 10.0 g, 72.9 mmol) with stirring, followed by dropwise addition of methyl iodide (5.5 mL, 87.5 mmol) at room temperature. After the addition was complete, the mixture was refluxed at 110° C. for 4 h. After being cooled to room temperature, water (300 mL) was added to the solution, the organic layer was separated, and the aqueous layer was extracted with EtOAc (3×150 mL). The combined organic layer was dried over anhydrous $MgSO_4$. The dried organic solution was filtered and concentrated under reduced pressure. The residue was purified by column chromatography on silica gel (hexane:EtOAc=5:2) to afford COOH—NHMe (IV) (6.95 g, 63%) as white solid. $^1$H NMR (400 MHz, DMSO-$d_6$, 298 K) δ (ppm): 7.77 (dd, J=12.0, 4.0 Hz, 1H), 7.40-7.35 (m, 1H), 6.67 (d, J=8.0 Hz, 1H), 6.55 (t, J=8.0 Hz, 1H), 2.83 (s, 3H); 13 C NMR (100 MHz, DMSO-$d_6$, 298 K) δ (ppm): 169.90, 151.68, 134.47, 131.55, 113.92, 110.67, 109.88, 29.16. The molecular structure (X-ray) of the synthesized compound IV is shown in FIG. 1(b), which is in a planar configuration.

COMPARATIVE EXAMPLES

Synthesis of 2-acetamidobenzoic acid (COOH—NHAc, Compound V)

To a solution of anthranilic acid (2.0 g, 14.6 mmol) in THF (30 mL), acetic anhydride (1.6 mL, 16.8 mmol) was added with stirring and the resulting mixture was then heated to reflux for 1 h. After being cooled to room temperature, the reaction mixture was poured into water (100 mL), and the aqueous layer was extracted with ethyl acetate (3×50 mL). The combined organic layer was dried over anhydrous $MgSO_4$. The dried organic solution was filtered and concentrated under reduced pressure. The residue was purified by column chromatography on silica gel (hexane:EtOAc=2:1) to afford COOH—NHAc (V) (1.88 g, 72%) as white solid. $^1$H NMR (400 MHz, DMSO-$d_6$, 298 K) δ (ppm): 13.57 (b, 1H), 11.05 (b, 1H), 8.45 (dd, J=12.0, 4.0 Hz, 1H), 7.96 (dd, J=12.0, 4.0 Hz, 1H), 7.57 (t, J=8.0 Hz, 1H), 7.14 (t, J=8.0 Hz, 1H), 2.12 (s, 3H); $^{13}$C NMR (100 MHz, DMSO-$d_6$, 298 K) δ (ppm): 169.45, 169.43, 140.83, 133.95, 131.01, 122.51, 119.92, 116.48, 24.98.

Synthesis of 2-(2,2,2-trifluoroacetamido)benzoic acid (COOH—$NHCOCF_3$, Compound VI)

To a stirred solution of anthranilic acid (1.87 g, 13.6 mmol) in THF (30 mL), trifluoroacetic anhydride (2.4 mL, 17.3 mmol) was added at 0° C. and the resulting mixture was then stirred at room temperature for 16 h. Until the end of the reaction, the solvent was concentrated under reduced pressure to give a white powder. The residue was dissolved in ethyl acetate, washed with saturated NaCl aqueous solution, and dried over anhydrous MgSO$_4$. The dried organic solution was filtered and concentrated under reduced pressure. The residue was purified by column chromatography on silica gel (hexane:EtOAc=5:2) to afford COOH—NHCOCF$_3$ (compound VI) (1.85 g, 58%) as white solid. $^1$H NMR (400 MHz, DMSO-d$_6$, 298 K) δ (ppm): 12.50 (brs, 1H), 8.27 (d, J=8.0 Hz, 1H), 8.05 (d, J=8.0 Hz, 1H), 7.71 (m, 1H), 7.36 (t, J=8.0 Hz, 1H); 13 C NMR (100 MHz, DMSO-d$_6$, 298 K) δ (ppm): 169.3, 154.8, 154.4, 154.1, 153.7, 137.5, 134.3, 131.3, 125.5, 121.3, 119.9, 119.3, 117.0, 114.2, 111.3; 19 F NMR (376 MHz, DMSO-d$_6$, 298 K) δ (ppm): −75.67.

Synthesis of
2,2,2-trifluoro-N-(2-formylphenyl)acetamide
(CHO—NHCOCF$_3$, Compound VII)

To a cold solution of 2-aminobenzaldehyde (0.225 g, 1.86 mmol) in anhydrous CH$_2$Cl$_2$ (15 mL) was added anhydrous pyridine (0.3 mL, 3.72 mmol), followed by dropwise addition of trifluoroacetic anhydride (0.336 mL, 2.42 mmol). After the addition was complete, the resulting mixture was warmed to room temperature and stirred in the same temperature for additional 4 h. Until the end of the reaction, 1M HCl (5 mL) was added to the solution, the organic layer was separated, and the aqueous layer was extracted with CH$_2$Cl$_2$ (3×10 mL). The combined organic layer was dried over anhydrous MgSO$_4$. The dried organic solution was filtered and concentrated under reduced pressure. The residue was purified by column chromatography on silica gel (hexane:CH$_2$Cl$_2$=5:1) to afford CHO—NHCOCF$_3$ (VII) (0.286 g, 71%) as white solid. $^1$H NMR (400 MHz, DMSO-d$_6$, 298 K) δ (ppm): 11.94 (b, 1H), 10.04 (s, 1H), 8.05 (d, J=12.0 Hz, 1H), 7.99 (dd, J=12.0, 4.0 Hz, 1H), 7.79 (m, 1H), 7.53 (m, 1H); $^{13}$C NMR (100 MHz, DMSO-d$_6$, 298 K) δ (ppm): 194.39, 155.68, 155.31, 154.94, 154.57, 136.58, 135.56, 133.67, 126.46, 125.74, 122.49, 119.87, 117.00, 114.13, 111.26; 19 F NMR (376 MHz, DMSO-d$_6$, 298 K) δ (ppm): −75.32; HRMS (EI) m/z: [M+] calc'd for C$_9$H$_6$F$_3$NO$_2$ [217.0351]; found 217.0351.

Synthesis of (2-(methylamino)phenyl)methanol
(Compound VIII, an Intermediate)

Methyl N-methylanthranilate (6.42 g, 38.9 mmol) in dry THF (25 mL) was added rapidly to a stirred solution of lithium aluminum hydride (LAH, 2.4 M in THF, 24.3 mL, 58.2 mmol) in dry THF (100 mL) at −78° C. by a cannula. The reaction mixture was warmed to room temperature and stirred in the same temperature for additional 5h. Until the end of the reaction, water (100 mL) was slowly added to the solution. The aqueous layer was extracted with EtOAc (3×100 mL). The combined organic layers were dried over MgSO$_4$. The dried solution was filtered and concentrated under reduced pressure. The residue was purified by column chromatography on silica gel (hexane:EtOAc=5:2) to afford S1 (3.26 g, 61%) as colorless oil. $^1$H NMR (400 MHz, DMSO-d$_6$, 298 K) δ (ppm): 7.10 (m, 2H), 6.57 (t, J=8.0 Hz, 1H), 6.52 (d, J=8.0 Hz, 1H), 5.13 (m, 1H), 5.07 (t, J=4.0 Hz, 1H), 4.41 (d, J=4.0 Hz, 2H), 2.73 (d, J=4.0 Hz, 3H); 13 C NMR (100 MHz, DMSO-d$_6$, 298 K) δ (ppm): 147.4, 128.0, 127.3, 125.7, 115.2, 108.8, 61.2, 29.9.

Synthesis of 2-(methylamino)benzaldehyde
(CHO—NHMe, Compound IX)

(2-(methylamino)phenyl)methanol (compound VIII, 0.43 g, 3.17 mmol) in dry DCM (8 mL) was added rapidly to a stirred solution of manganese(IV) oxide (MnO$_2$, 1.1 g, 12.66 mmol) in dry DCM (12 mL) by a cannula. Kept the reaction temperature at 30° C. for 18 h. After being cooled to room temperature, the reaction mixture was filtrated, and the combined organic layers were concentrated under reduced pressure. The residue was purified by column chromatography on silica gel (hexane:EtOAc=5:1) to afford the matrix compound (0.27 g, 63%) as yellow oil. $^1$H NMR (400 MHz, DMSO-d$_6$, 298 K) δ (ppm): 9.80 (s, 1H), 8.14 (b, 1H), 7.58 (dd, J=12.0, 4.0 Hz, 1H), 7.45 (t, J=8.0 Hz, 1H), 6.70 (m, 2H), 2.86 (d, J=4.0 Hz, 3H); $^{13}$C NMR (100 MHz, DMSO-d$_6$, 298 K) δ (ppm): 194.0, 150.8, 136.5, 135.9, 118.0, 114.5, 110.5, 28.8; LRMS (EI) m/z: [M+] calc'd for C$_8$H$_9$NO [135.1]; found 135.1.

Notably, the reactions adopted in this study are facile and produce title molecules with good yields (>50%). The matrix compounds I to IV in the Examples were rationally designed for the carboxylic carbonyl group and amino derivatives to be in the ortho position in order to form an intramolecular hydrogen bond (H-bond) between the carboxylic/carbonyl and amino hydrogen. It should be noted that for compound I and compound IV, the carboxylic and amino groups that serve as proton donor and proton acceptor, respectively, are to effectively produce positive and negative ions. The above strategy has two major characteristics. First, the intramolecular H-bond induced π-conjugation, which decreases the HOMO-LUMO energy gap to reach the absorption maximum suitable for commercial laser excitation (third harmonic Nd:YAG laser, 355 nm). Second, the formation of intramolecular H-bond is to reduce the intermolecular H-bond interaction and thus to increase the efficiency of the desorption.

Figure 2A:
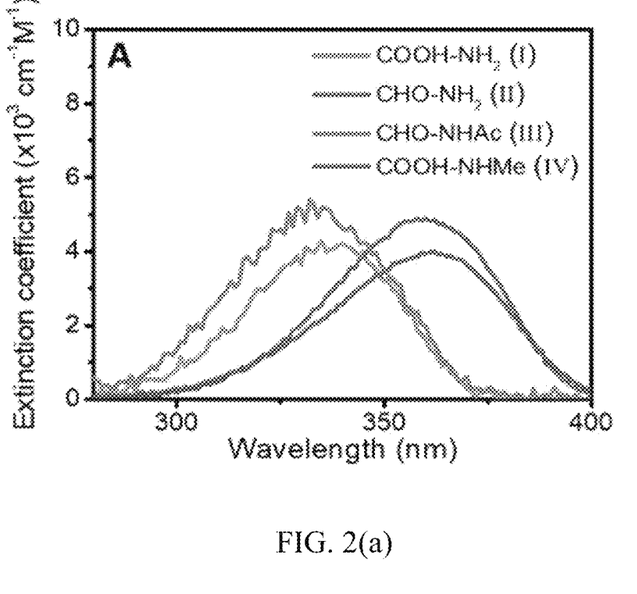
FIG. 2(a) shows absorption spectra of the anthranilic derivatives used in the present disclosure measured in dichloromethane.
Figure 2B:
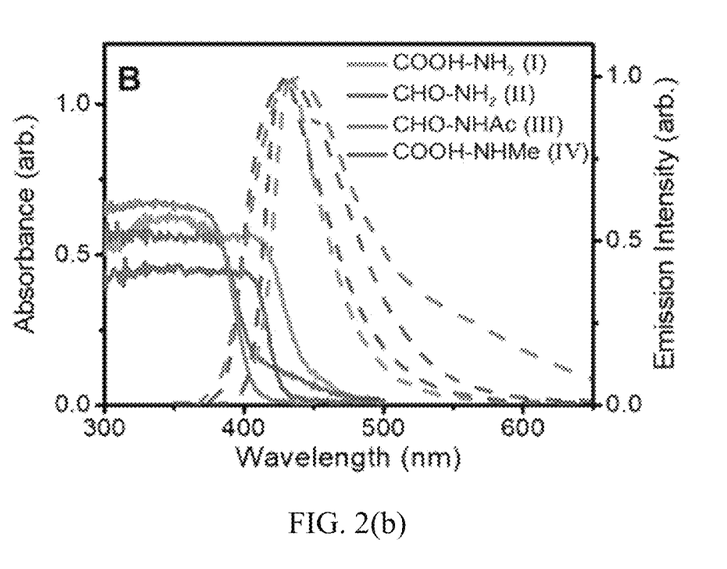
FIG. 2(b) shows absorption spectra and emission spectra of anthranilic derivatives used in the present disclosure measured in solid state.

The absorption spectra and the emission spectra of the matrix compounds I to IV are shown in FIGS. 2(a) and 2(b). FIG. 2(a) shows the absorption spectra of matrix compounds I to IV measured in dichloromethane (DCM). All of the matrix compounds I to IV exhibit the lowest lying absorption bands in the range of 300 nm to 400 nm. Appreciable absorption extinction of >2000 cm$^{-1}$ M$^{-1}$ was observed for all I-IV at 355 nm of the third harmonic Nd:YAG laser, the most popular commercial excitation source for MALDI. Among the matrix compounds I to IV, COOH—NHMe (compound IV) exhibits the highest extinction coefficient at 355 nm.

It is also worth noting that, in the matrix compounds used in the present disclosure, the formation of intramolecular H-bond is to enhance the charge transfer character and hence the red shift of the absorption. For example, anchoring carboxyl and amino groups in meta- and para-positions with no intramolecular H-bond formation cause the blue shift of the absorption with peak wavelength being far blue-shifted from 355 nm.

Aside from matrix compounds I to IV, other anthranilic derivatives have also been synthesized (see Comparative examples, matrix compounds V to IX). However, those compounds show either unsuitable absorption band (V to VIII) or low melting points (IX) and are not suitable for the purpose of the present disclosure.

FIG. 2(b) shows the absorption (solid line) and emission spectra (dash line) of matrix compounds I to IV measured in solid state. The excitation wavelength is 340 nm for matrix compounds I, II and IV and is 320 nm for matrix compound III. The different absorption pattern of matrix compounds I to IV between solution and solid phase suggests slightly intermolecular interaction existing in solid state.

As described above, the use provided by the present disclosure includes step (b) applying the matrix compound and an analyte onto a sample holder.

Specifically, the matrix compounds used in the present disclosure are applied and used in different approaches, depending on the type of the analyte and the analyzing process. For example, in the case that the analyte is lipid and protein, a solution of the matrix compound and a solution including the lipid or protein may be prepared separately in advance, and these solutions may then be mixed and applied onto a sample holder. Specifically, in some embodiment of the present disclosure, the step of applying the matrix compound and the analyte onto the sample holder further comprises mixing the matrix compound with a solvent to form a matrix solution; mixing the matrix solution with the analyte to form a sample mixture; and applying the sample mixture onto the sample holder.

In an embodiment of the present disclosure, the analyte may comprise biological tissues, such as mouse brain extract. In a preferable embodiment, the solvent comprises acetonitrile and water in a ratio of 0.5 to 2:1 (v/v). In a more preferable embodiment, the solvent comprises acetonitrile and water in a ratio of 1:1 (v/v). In a preferable embodiment, the step of mixing the matrix solution with the analyte, the matrix solution and the analyte are mixed in a ratio of 0.5:1, 0.75:1, 1:1, 1.25:1 or 1.5:1 by volume. However, the present disclosure is not limited thereto.

It should be noticed that the pH of the matrix solution may be adjusted before applying onto the sample holder. In and exemplified example, COOH—NHMe (compound IV) and COOH—$NH_2$ (compound I) were dissolved in acetonitrile and water (1:1, v/v) at a concentration of 0.1 M. The pH values of matrix solutions are around 4. Trifluoroacetic acid (TFA) and ammonium hydroxide ($NH_4OH$) may be used to adjust the pH value of those matrix solutions. Because COOH—NHMe (compound IV) and COOH—$NH_2$ (compound I) are zwitterionic and weak acid, they work as buffering agents. However, the pH-adjustment procedure may be performed based on actual needs.

As another example, in a case that the matrix compounds used in the present disclosure are used to perform MALDI-Mass MSI, the step of applying the matrix compound and the analyte onto the sample holder may further comprises depositing the analyte onto the sample holder; and depositing the matrix compound onto the sample holder. In other words, the analyte and the matrix compound are not mixed before being applied onto the sample holder. The analyte, such as a sectioned mouse brain, may be thaw-mounted onto the sample holder, such as a ITO-coated glass slide, and the matrix compounds may be deposed onto the sample. In a preferable embodiment, the matrix compound is deposited onto the sample holder by an evaporation deposition process. For example, the sublimation for the matrix compound may be carried out under specific temperature and pressure for specific time. However, the present disclosure is not limited thereto. Some exemplified processes for preparing the sample to be disposed on the sample holder is described in detail herein.

Example of Sample Preparation

Sample Preparation for Lipid and Protein.

A 0.1 M solution of each matrix compounds I to IV was prepared in acetonitrile and water (1:1, v/v). Individual lipid solutions of PS(14:0/14:0), PE(14:0/14:0), and PC(14:0/14:0) at 0.2 mg/mL was prepared in chloroform and methanol (1:1, v/v). PC(14:0/14:0), PE(14:0/14:0), PA(14:0/14:0), PS(14:0/14:0), and phosphatidylglycerol PG(14:0/14:0) were purchased from Avanti Polar Lipids, Inc(Alabaster, Ala.). A lipid mixture of PS(14:0/14:0), PE(14:0/14:0), PC(14:0/14:0), PA(14:0/14:0), and PG(14:0/14:0) was prepared at the same concentration and in the same solvent system. The protein calibration I kit (purchased from Bruker Daltonics (Bremen, Germany)) was dissolved in 150 μL of deionized water to make the protein mixture. The matrix and standard solutions were mixed 1:1 (v/v) and 1.4 μL of each mixture was spotted onto the sample plate and left to air-dry.

Tissue Preparation for Mouse Brain Extract.

Mouse brains were purchased from BioLASCO Taiwan Co., Ltd. (Taipei, Taiwan). Mouse brains were grounded into powder in liquid nitrogen. The powder was then mixed with MeOH/ACN/EA 10:7:3 (v/v/v) and sonicated for 15 min to extract the lipid species. One milliliter of the supernatant was transferred to a clean Eppendorf tube and concentrated to 250 μL under vacuum. The lipid extract was stored under −20° C. until needed. Like the standard profile, the matrix and extracts were mixed 1:1 (v/v) and 1.4 μL of the mixture was spotted onto the sample plate and air-dried. The remaining pellet after lipid removal was mixed with 1 mL water/ACN/TFA 50:50:1 (v/v/v) solution and sonicated for 2 min to extract the protein species. In this case, the supernatant was transferred to a clean Eppendorf tube and 1 mL of the supernatant was mixed with 10 mL of one of four saturated matrix solutions (COOH—NHMe, 2,5-DHB, 2,5-DHAP, and 1,5-DAN) for analysis. 2,5-DHB and 1,5-DAN are purchased from Tokyo Chemical Industry Co., Ltd. (Tokyo, Japan), and 2,5-DHAP is purchased from Alfa Aesar (Ward Hill, Mass.).

Tissue Preparation for MSI.

A mouse brain was sectioned at 12 μm thickness using a Leica CM1950 cryostat following a previously described protocol (as described in Lin, L.-E.; Su, P.-R.; Wu, H.-Y; Hsu, C.-C. J. Am. Soc. Mass Spectrom. 2018, 29, 796-799). In short, the tissue was sectioned at −20° C. and thaw-mounted onto a Indium tin oxide(ITO)-coated glass slide. The ITO-coated glass slides were purchased from Ruilong (Taichung, Taiwan). The slides were then stored under −80° C. until needed. After desiccation for more than thirty minutes (>30 min), sublimation was carried out using a home-built sublimation system where 0.5 mg/$cm^2$ of matrix was deposited onto the sample at 60° C. with a 0.7 Torr vacuum for 10 s.

The use provided by the present disclosure further includes step (c) analyzing the analyte by the MALDI mass spectrometer. In a preferable embodiment, the step of analyzing the analyte by the MALDI mass spectrometer comprises performing at least one of a MALDI-TOF mass analyzing procedure and a MALDI-TOF mass spectrometry imaging analyzing procedure. In a more preferable embodiment, the step of analyzing the analyte by the MALDI mass spectrometer comprises performing both of a MALDI-TOF mass analyzing procedure and a MALDI-TOF mass spectrometry imaging analyzing procedure.

In an embodiment of the present disclosure, the step of analyzing the analyte by the MALDI mass spectrometer is performed in both positive ion mode and ion negative mode. In a preferable embodiment of the present disclosure, the positive ion mode has a detector gain of 1800V to 2050 V, and the negative ion mode has a detector gain of 1800V to 2050 V. In a most preferable embodiment of the present disclosure, the positive ion mode has a detector gain of 1837V, and the negative ion mode has a detector gain of 1841V. However, the detector gains of the positive and negative ion modes may be adjusted based on the experimental needs and are not limited in the present disclosure.

In an embodiment of the present disclosure, the MALDI mass spectrometer includes a Nd:YAG laser as an excitation source. The Nd:YAG laser may have a wavelength of 355 nm. In a preferable embodiment of the present disclosure, a raster size of a laser operating poser of the MALDI mass spectrometer is from 80 μm to 150 μm. An exemplified example of the details of the MALDI-TOF Mass spectrometry is provided below.

Both MALDI-TOF MS and MALDI-TOF MSI were performed on a Bruker Autoflex Speed mass spectrometer in reflectron geometry at 1 kHz repetition rate.

MALDI-TOF MS

For profiling, mass spectra were obtained by accumulating 1000 to 1500 laser shots with the "random walk" setting. The detector gain was set at 2016 V for positive mode and 2012 V for negative mode. However, the present disclosure is not limited thereto and the numbers of laser shots and the detector gains may be adjusted according to actual needs.

MALDI-TOF MSI

Mass spectrometry images (MSI) were acquired at 80 to 150 μm spatial resolution with 100, 300, 500, 1000 or 1500 laser shots per pixel, with the laser operating power at 50% and a 1 kHz repetition rate.

However, in a preferable embodiment, the MSI were accumulated at 100 laser shots per pixel and at a 1 kHz repetition rate. In such embodiment, the positive ion mode has a detector gain of 1837V, and the negative ion mode has a detector gain of 1841V. It should be noted that under such parameters, the MSI may result in good intensity.

As an example, the laser spot size was set at "medium", ~80 μm in diameter. The measurement order was set at Fast (from top to bottom). The imaging results shown were normalized by total ion counts (TIC). Image acquisition was carried out using FlexImaging 3.0, and spectral analysis was performed with FlexAnalysis 3.4.

Next, the effectiveness of the matrix compounds provided by the present disclosure is described in details herein. Matrix compounds I to IV are used as the matrix, and PS(14:0/14:0) mentioned above is used as the analyte to demonstrate the 355 nm laser desorption property.

Figure 3:
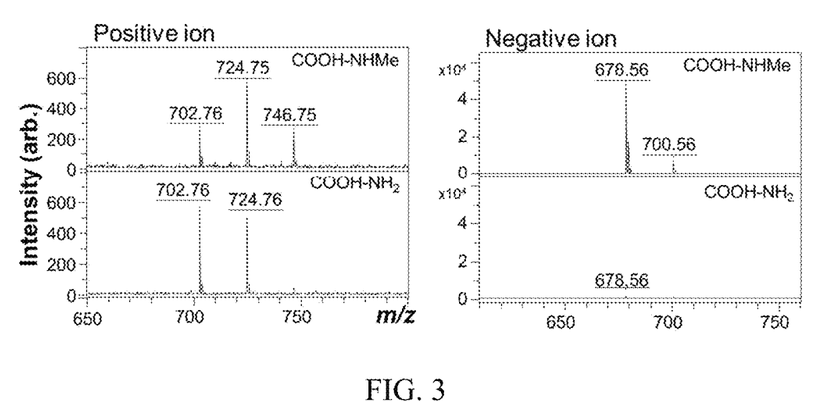
FIG. 3 shows mass spectra of lipids obtained from samples prepared with the matrix compound of the present disclosure in positive and negative ion modes.

Reference is made to FIG. 3. FIG. 3 shows mass spectra of lipids obtained from samples prepared with the matrix compounds I and IV of the present disclosure in positive and negative ion modes. As shown in FIG. 3, compound IV (COOH—NHMe) demonstrates a high ion signal due to its strongest absorption at 355 nm (as shown in FIG. 2(a)), suggesting that the ion efficiency is highly related to the extinction coefficient. Moreover, the characteristic signals for PC(14:0/14:0), PS(14:0/14:0) and PE(14:0/14:0) were most strongly detected by COOH—$NH_2$ (compound I) and COOH—NHMe (compound IV) (as demonstrated in FIG. 3).

The inventors of the present disclosure found that the above experimental results do not align with the extinction coefficient of the matrix: COOH—NHMe (compound IV)>CHO—$NH_2$ (compound II)>CHO—NHAc (compound III)>COOH—$NH_2$ (compound I). This may due to the fact that the extinction coefficient merely accounts for one of multiple factors for analyte desorption/ionization, and other factors, such as the difference in fluorescence lifetime among matrix compounds I to IV also need to be considered. Because the applied 355 nm laser used in the present disclosure has a pulse duration time of about 5 ns, matrices with longer fluorescence lifetime, such as COOH—$NH_2$ (compound I) and COOH—NHMe (compound IV), have a higher chance for multiphoton events. More importantly, matrix interaction with analyte is worth noting when it comes to the MALDI process.

Generally, positive ions are observed as protonated, sodiated or potassiated ions ($[M+H]^+$, $[M+Na]^+$, and $[M+K]^+$), where negative ions are observed as deprotonated ions ($[M-H]^-$). Therefore, in order to quantify the feasibility of the synthesized matrix, theoretical calculation based on density function theory (DFT) was conducted to acquire the corresponding proton affinity (PA) and deprotonation energy (DE), whose values provide insights into the tendency toward producing $[M+H]^+$ and $[M-H]^-$, respectively. Table 1 shows Heat (kcal/mol) of protonation, deprotonation, and proton transfer reaction for the compounds in the gas phase (Calculated results are from DFT). Absorption characteristics at 355 nm are considered. Among the synthesized matrix compound, COOH—NHMe (compound IV) demonstrated relatively high PA and low DE (see Table 1 below), and thus is a suitable matrix in both positive and negative modes. Notably, the values of PA and DE of COOH—NHMe (compound IV) are comparable to those of commercial matrices that are solely suitable in either positive or negative mode, showing its high potential in practical matrix applications.

TABLE 1

| Matrix compound | Proton affinity (kcal/mol) $M + H^+ \rightarrow [M+H]^+$ | Deprotonation energy (kcal/mol) $M \rightarrow [M-H]^- + H^+$ | Proton transfer reaction (kcal/mol) $M + M \rightarrow [M+H]^+ + [M-H]^-$ | Extinction coefficient[b] ($cm^{-1}M^{-1}$) |
|---|---|---|---|---|
| COOH—$NH_2$ (compound I) | 207 | 336 | 129 | 2400 |
| CHO—$NH_2$ (compound II) | 205 | 362 | 157 | 3800 |
| CHO—NHAc (compound III) | 197 | 349 | 152 | 2600 |
| COOH—NHMe (compound IV) | 219 | 333 | 114 | 4800 |
| COOH—$NHCOCF_3$ (compound VI) | 190 | 317 | 127 | 60 |
| CHO—$NHCOCF_3$ (compound VII) | 189 | 335 | 146 | 390 |

TABLE 1-continued

| Matrix compound | Proton affinity (kcal/mol) M + H⁺ →[M + H]⁺ | Deprotonation energy (kcal/mol) M→[M − H]⁻ + H⁺ | Proton transfer reaction (kcal/mol) M + M→ [M + H]⁺ + [M − H]⁻ | Extinction coefficient[b] (cm⁻¹M⁻¹) |
|---|---|---|---|---|
| CHCA | 197 [a] | 316 [a] | 119 [a] | 13000 |
| 2,5-DHB | 202, 200 [a] | 323, 325 [a] | 121, 120 [a] | 2200 |
| 2,5-DHAP | 209 [a] | 338 [a] | 129 [a] | 1100 |
| 9-AA | 204 | 340 | 136 | 2100 |
| 1,5-DAN | 216 | 358 | 142 | 1100 |

[a] Calculated results are from ab initio quantum chemistry calculations.
[b] All compounds were dissolved in DCM for UV-visible measurement.

Figure 4:
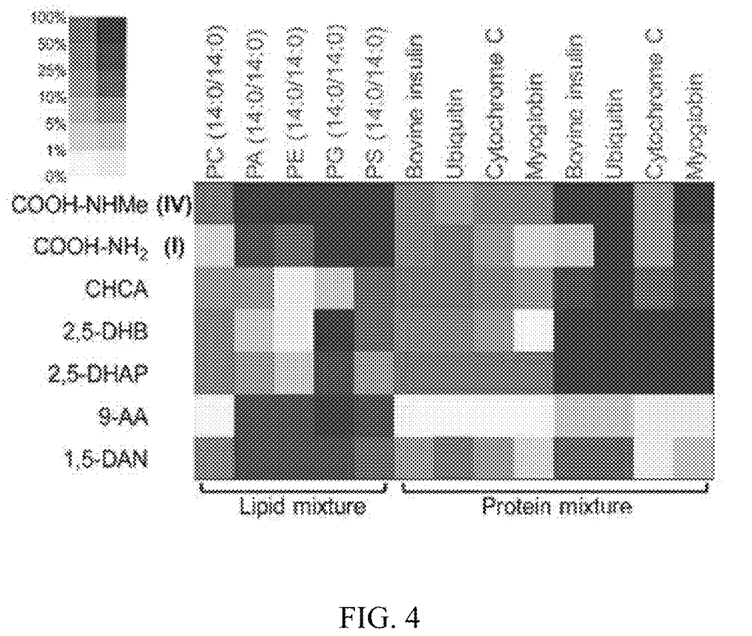
FIG. 4 shows a schematic view illustrating the comparison of the relative signal intensities of lipid species and protein species when using the anthranilic acid derivatives of the present disclosure and some of the most representative commercially available matrices.

To gain more insight into the efficacy of the matrix compound used in the present disclosure, the inventors choose some of the most representative commercially available matrices to compare their performances. Reference is made to FIG. 4. FIG. 4 is a schematic view showing the comparison of the relative signal intensities of lipid species and protein species when using the anthranilic acid derivatives of the present disclosure (matrix compounds I to IV) and some of the most representative commercially available matrices.

Specifically, FIG. 4 shows the relative signal intensities of different lipids (PC(14:0/14:0), PS(14:0/14:0), and PE(14:0/14:0)) and different proteins from different matrix compound. As shown in FIG. 4, 2,5-DHB and CHCA provide lower ion abundance of negative ion relative to positive ion, and are commonly used in positive ion detection. On the other hand, 9-AA and 1,5-DAN are suitable for negative ion detection. In comparison, the signal intensities of lipid and protein standards detectable with the COOH—NH₂ (compound I) and COOH—NHMe (compound IV) are great candidates of MALDI matrices for dual polarity detection.

As shown in FIG. 4, it is noticed that lipids analyzed using COOH—NHMe (compound IV) as the matrix compound exhibited the highest ion signal compared to other compounds, even though the extinction coefficients of all studied matrices were within the same order of magnitude. The most comparative commercially available matrix was 1,5-DAN for lipid detection, though its protein signals were less impressive.

Figure 5:
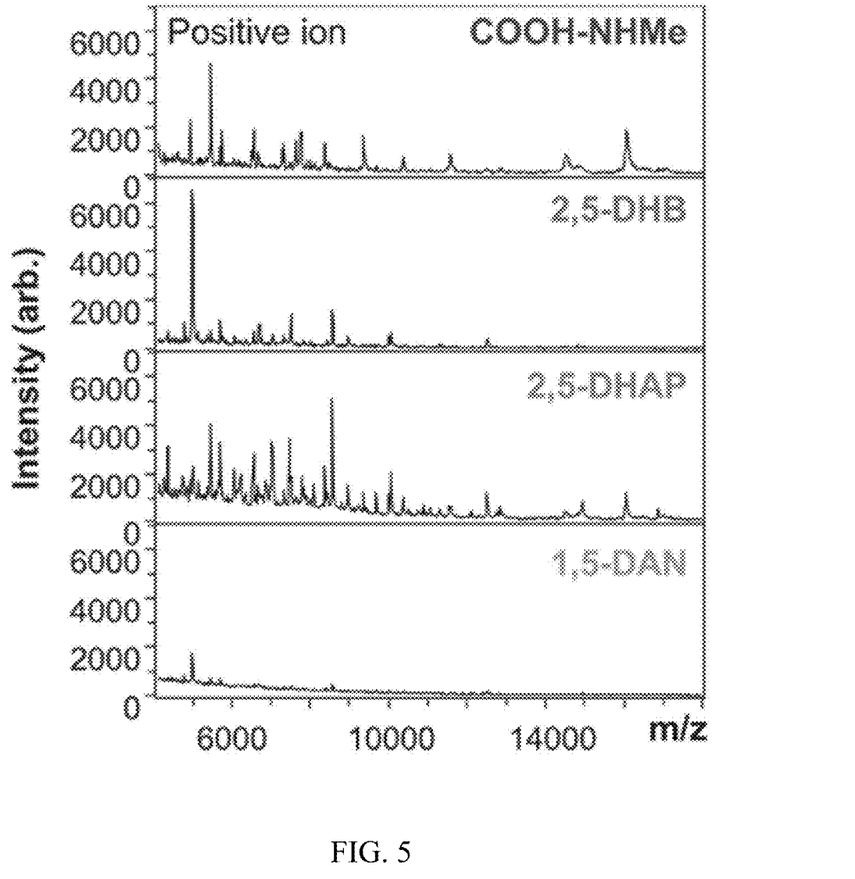
FIG. 5 shows mass spectra of the brain protein extracts obtained from samples prepared by an anthranilic acid derivative of the present disclosure and commonly used commercial matrices for protein analysis in positive ion mode.

Reference is made to FIG. 5. FIG. 5 shows mass spectra of the brain protein extracts obtained from samples prepared by an anthranilic acid derivative of the present disclosure and commonly used commercial matrices for protein analysis in positive ion mode. As shown in FIG. 5, a great number of protein species were observed with COOH—NHMe (compound IV) and 2,5-DHAP relative to 2,5-DHB. Moreover, relatively few protein species may be observed from 1,5-DAN, implying that this previously reported dual polarity matrix may have limited mass coverage for biomolecules.

Figure 6:
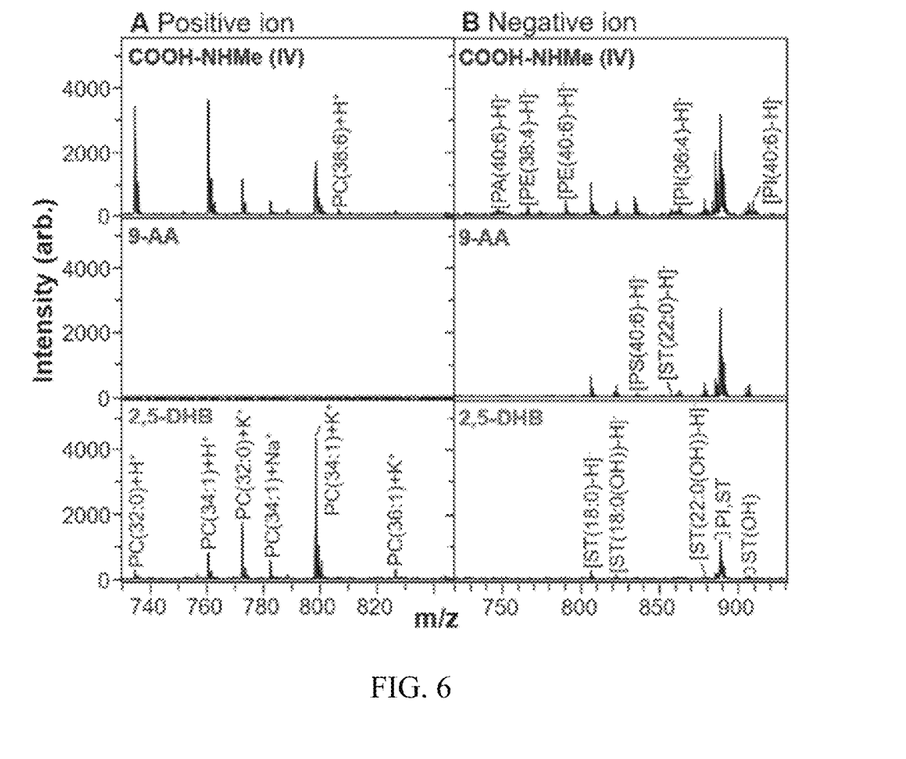
FIG. 6 shows mass spectra of the brain lipid extract obtained from samples prepared by an anthranilic acid derivative of the present disclosure and commonly used commercial matrices for lipid analysis in positive and negative ion mode.

Reference is made to FIG. 6. FIG. 6 shows Mass spectra of the brain lipid extract obtained from samples prepared by an anthranilic acid derivative of the present disclosure and commonly used commercial matrices for lipid analysis in positive and negative ion mode. It should be noted that in FIG. 6, the ions marked in red indicate that the ions observed only using COOH—NHMe (IV) as matrix. The ions observed using 9-AA as matrix but not 2,5-DHB were marked in blue. The superiority of COOH—NHMe (IV) in terms of the molecular coverage and dual-polarity compatibility in the MALDI-TOF measurement on mouse brains lipid extract are demonstrated herein.

To be specific, as shown in FIG. 6, COOH—NHMe (compound IV) outperformed the widely used commercial matrices for lipid analysis in both positive and negative mode. Remarkably, COOH—NHMe (compound IV) showed a rich lipid profile in both positive and negative ion mode, whereas 2,5-DHB and 9-AA showed only limited coverage due to their single-polarity character.

The positive (deprotonation of the matrix) and negative (protonated of the matrix) may be explained by the proton affinity and deprotonation energy of the matrix compounds (see Table 1). The deprotonation energy of 2,5-DHB is relatively low, so the proton transfers easily from matrix to analyte, producing protonated analyte ion. On the contrary, the proton affinity of 9-AA is relatively high and the proton easily transfers from analyte to matrix, yielding deprotonated analyte ions. The left side of FIG. 6 (marked as A positive ion) shows the signals of the positive ions, [M+H]⁺, [M+Na]⁺, and [M+K]⁺. In the right side of FIG. 6 (marked as B negative ion), signals of negative ion represent [M−H]⁻ corresponding to phosphatidylethanol-amines (PE), phosphatidic acids (PA), phosphatidylserines (PS), phosphatidylinositols (PI) sulfatides (ST), and hydroxylated sulfatides (ST(OH)) are shown.

Furthermore, LC-MS/MS was conducted on the sample mouse brain extract, and the species detected were confirmed by LipidSearch (Thermo Fisher Scientific). The assignments of mass spectra show that the results obtained by using COOH—NHMe (compound IV) as a matrix revealed more lipid species than using 2,5-DHB and 9-AA. For example, [PE(40:6)-H]⁻, [PI(36:4)-H]⁻ and [PI(40:6)-H]⁻ were observed when COOH—NHMe (compound IV) was used as the matrix but missing when using 2,5-DHB.

Figure 7:
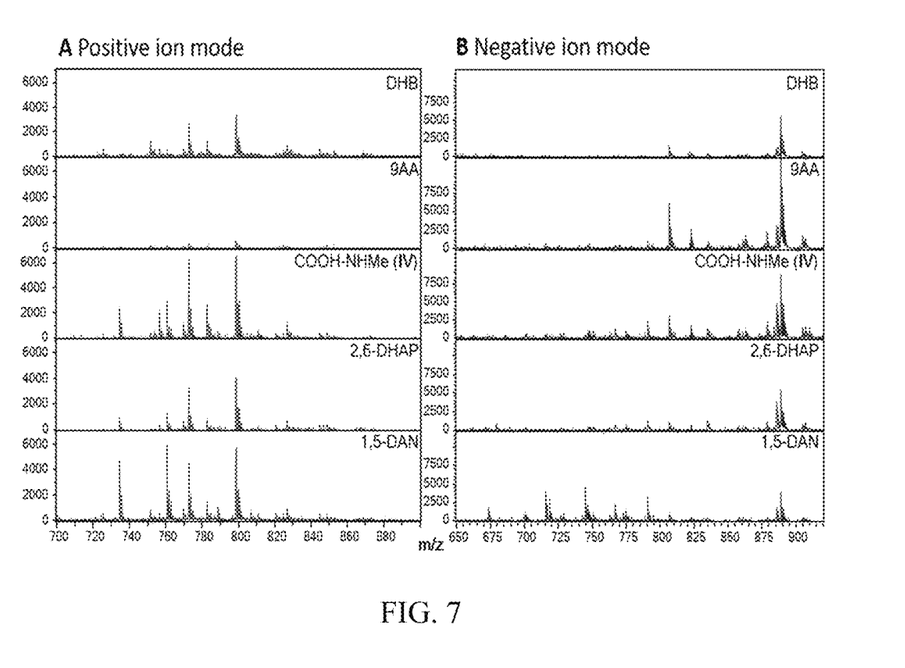
FIG. 7 shows mass spectra of the brain lipid extract obtained from samples prepared by existing matrix compounds and a matrix compound of the present disclosure, in both positive and negative ion mode.

Reference is made to FIG. 7. FIG. 7 shows mass spectra of the brain lipid extract obtained from samples prepared by 2,5-DHB, 9-AA, COOH—NHMe (compound IV), 2,6-DHAP and 1,5-DAN, in (A) positive and (B) negative ion mode respectively. The comparison between COOH—NHMe (compound IV) and early reported matrices for dual polarity has been made. As a result, the performance of COOH—NHMe (IV) is as good as 2,6-DHAP and 1,5-DAN in both positive and negative ion mode. However, it should be noted that due to the limited vacuum stability, 2,6-DHAP is not commonly applied for vacuum MALDI MSI, but instead used for atmospheric pressure (AP)-MALDI.

Figure 8:
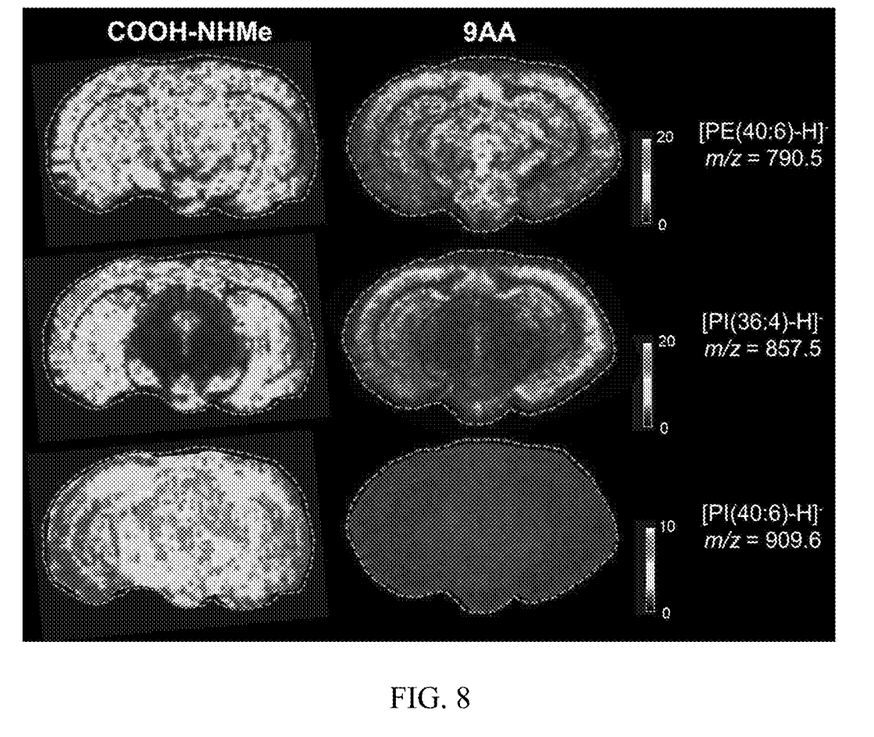
FIG. 8 shows MSI of mouse brains sections sublimated with an anthranilic acid derivative of the present disclosure and a commonly used commercial matrix in negative ion mode.

Reference is made to FIG. 8. FIG. 8 shows MSI of mouse brains sections sublimated with an anthranilic acid derivative of the present disclosure and a commonly used commercial matrix in negative ion mode. In FIG. 8, the color scale for each ion species were under the same intensity threshold. The lipid species scan revealed the deprotonated ion at m/z 790.5, 857.5 and 909.6, corresponding to [PE(40:6)-H]⁻, [PI(36:4)-H]⁻ and [PI(40:6)-H]⁻, respectively.

Figure 9:
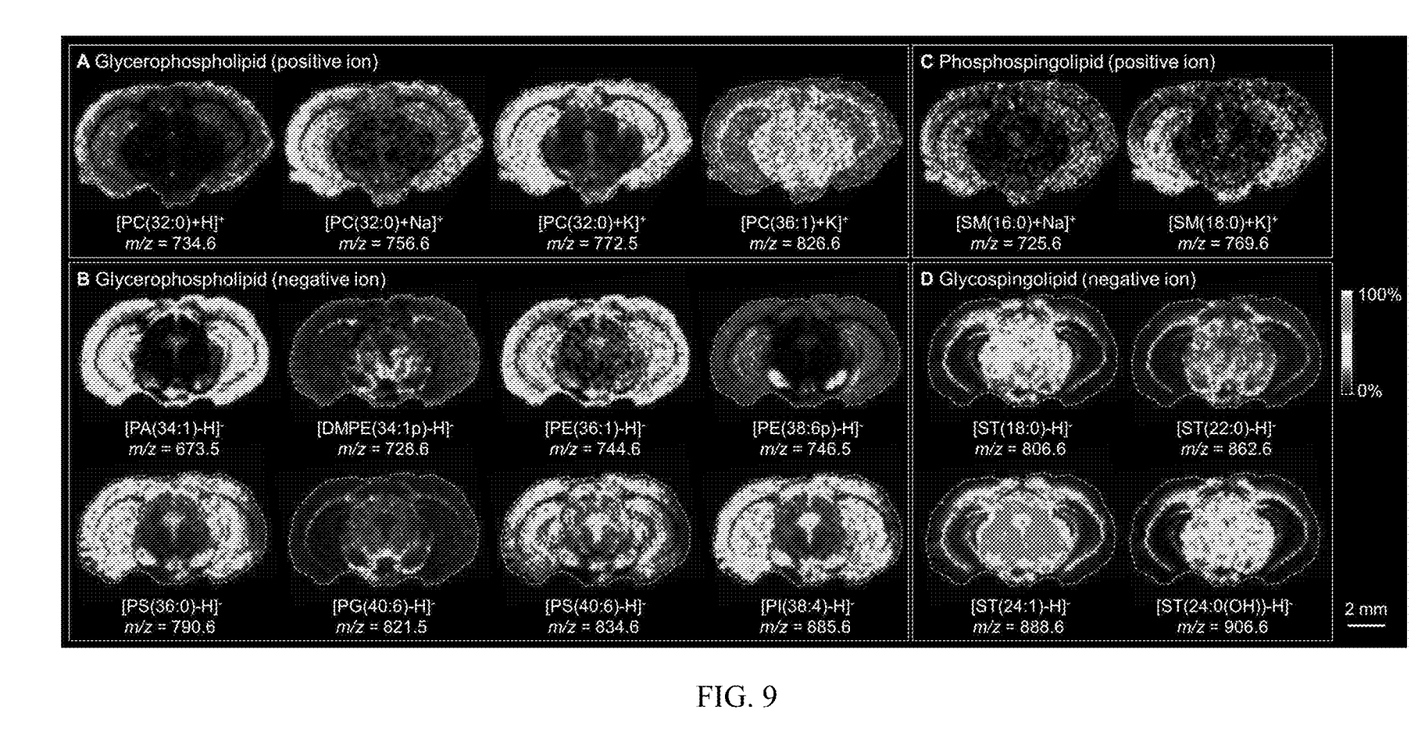
FIG. 9 shows MSI of mouse brain sections sublimated with COOH—NHMe (IV) in positive and negative ion mode at 150 μm spatial resolution.

Reference is made to FIG. 9. FIG. 9 shows MSI of mouse brain sections sublimated with COOH—NHMe (IV) in positive and negative ion mode at 150 μm spatial resolution. In FIG. 9, glycerophospholipids are observed in both (A) positive and (B) negative ion modes, phosphosphingolipids are observed in positive ion mode (C), and glycosphingolipids are observed in negative ion mode (D). Both positively charged and negatively charged lipid species were observed using common sublimation method.

Specifically, to demonstrate the capability of COOH—NHMe (compound IV) in mapping the lipid distribution, the matrix compound IV is applied as the matrix for MALDI-TOF MSI on a coronal mouse brain section. As shown in FIG. 9, in the positive ion mode, PC and sphingomyelin (SM) species were observed, in which PC (36:1) was largely observed in the white matter of the brain, whereas PC (32:0) was revealed in the gray matter. In the negative ion mode, several glycerophospholipids were observed, for example, PA (34:1), PE (36:1), PS (36:0), PI (38:4) in the gray matter and the dimethyl-phosphatidylethanolamine DMPE (34:1p), PG (40:6) in the white matter. ST was also resolved in the negative ion mode. As such, similar to the analysis of the brain lipid extract, untargeted molecular imaging of lipids is successfully obtained by MALDI-TOF MSI with both positive ions and negative ions simultaneously within one experiment.

In addition, using matrix compound (IV) as matrix for a MALDI Mass spectrometry may perform high spatial resolution MSI. Given that sublimation produces subnanometer crystals, with a more advanced system such as the Bruker rapifleX equipped with a 10 kHz laser, it may accomplish 5 μm MSI on an entire mouse brain section within 2 h.

In sum, the present disclosure provides a use of an anthranilic acid derivative as a matrix for a MALDI Mass spectrometry which comprises the use of a matrix compound represented by the following formula:

wherein X is selected from hydrogen and a hydroxyl group, and Y is selected from hydrogen, a methyl group or an acetyl group, provided that when X is hydrogen, Y is hydrogen or an acetyl group, and when X is a hydroxyl group, Y is a methyl group.

In the above chemical formula, when X and Y are both hydrogen (H), the matrix compound is 2-aminobenzaldehyde (compound II). When X is hydrogen and Y is an acetyl group, the matrix compound is N-(2-formylphenyl)acetamide (compound III). When X is a hydroxyl group and Y is a methyl group, the matrix compound is 2-(methylamino) benzoic acid (compound IV).

Specifically, the matrix compounds used in the present disclosure are suitable for candidates of a matrix for a MALDI Mass spectrometry. Among the matrix compounds I to IV, COOH—NH$_2$ (compound I) and COOH—NHMe (compound IV) are endowed with acid/base bifunctional properties for dual polarity detection in MALDI-TOF mass spectrometry. In other words, matrix compound I and IV are for the detection of both positive and negative ions in MALDI.

In addition, COOH—NHMe (compound IV) exhibits an outstanding efficiency in generating ions of a wide variety of biomolecules, including lipids and proteins, upon laser excitation. High quality molecular imaging of lipids in mouse brains sections was readily obtained by a commercial MALDI-TOF mass spectrometer using said matrix compound.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for providing a dual polarity sample for detecting biomolecules, said sample comprising a matrix compound and an analyte for processing by a MALDI Mass spectrometer, comprising:
   preparing the matrix compound comprising an anthranilic acid derivative represented by the following formula:

wherein X is selected from hydrogen and a hydroxyl group, and Y is selected from hydrogen, a methyl group or an acetyl group, provided that when X is hydrogen, Y is hydrogen or an acetyl group, and when X is a hydroxyl group, Y is a methyl group;
   applying the matrix compound and the analyte onto a sample holder to form the sample comprising the matrix compound and the analyte; and
   administering the sample holder with the sample comprising the matrix compound and the analyte to the MALDI mass spectrometer.

2. The method of claim 1, wherein X is hydrogen, and Y is hydrogen or an acetyl group.

3. The method of claim 1, wherein X is a hydroxyl group and Y is a methyl group.

4. The method of claim 1, wherein the analyte comprises lipids or proteins.

5. The method of claim 1, wherein the step of applying the matrix compound and the analyte onto the sample holder further comprises:
   mixing the matrix compound with a solvent to form a matrix solution;
   mixing the matrix solution with the analyte to form a sample mixture; and
   applying the sample mixture onto the sample holder.

6. The method of claim 5, wherein the solvent comprises acetonitrile and water.

7. The method of claim 5, wherein in the step of mixing the matrix solution with the analyte, the matrix solution and the analyte are mixed in a ratio of 0.5 to 1.5:1 by volume.

8. The method of claim 1, wherein the step of applying the matrix compound and the analyte onto the sample holder further comprises:
depositing the analyte onto the sample holder; and
depositing the matrix compound onto the sample holder.

9. The method of claim 8, wherein the analyte comprises biological tissues.

10. The method of claim 8, wherein the matrix compound is deposited onto the sample holder by an evaporation deposition process.

11. The method of claim 1, wherein by the MALDI mass spectrometer is configured to performing at least one of a MALDI-TOF mass analyzing procedure and a MALDI-TOF mass spectrometry imaging analyzing procedure.

12. The method of claim 1, wherein the MALDI mass spectrometer is configured to perform in both positive ion mode and ion negative mode.

13. The method of claim 12, wherein the positive ion mode has a detector gain of 1800V to 2050 V, and the negative ion mode has a detector gain of 1800V to 2050 V.

14. The method of claim 1, wherein the MALDI mass spectrometer includes a Nd:YAG laser with a wavelength of 355 nm as an excitation source.

15. The method of claim 14 wherein a raster size of a laser operating poser of the MALDI mass spectrometer is from 80 μm to 150 μm.

\* \* \* \* \*